United States Patent
Phillips

(10) Patent No.: US 10,429,331 B2
(45) Date of Patent: Oct. 1, 2019

(54) HEAT EXCHANGER MONITORING SYSTEM

(71) Applicant: HS Marston Aerospace Ltd., Wolverhampton, West Midlands (GB)

(72) Inventor: Paul Phillips, Bromsgrove (GB)

(73) Assignee: HS MARSTON AEROSPACE LTD., Wolverhampton (GB)

( * ) Notice: Subject to any disclaimer, the term of this patent is extended or adjusted under 35 U.S.C. 154(b) by 50 days.

(21) Appl. No.: 15/886,973

(22) Filed: Feb. 2, 2018

(65) Prior Publication Data
US 2018/0224387 A1    Aug. 9, 2018

(30) Foreign Application Priority Data
Feb. 8, 2017  (EP) ..................... 17155284

(51) Int. Cl.
| | |
|---|---|
| *G01N 27/22* | (2006.01) |
| *G01N 33/28* | (2006.01) |
| *F28F 27/00* | (2006.01) |
| *F28G 15/00* | (2006.01) |

(52) U.S. Cl.
CPC ............. *G01N 27/22* (2013.01); *F28F 27/00* (2013.01); *F28G 15/003* (2013.01); *F28F 2200/00* (2013.01)

(58) Field of Classification Search
CPC ......... G01N 27/22; G01N 33/28; F28F 27/00; F28G 15/003
See application file for complete search history.

(56) References Cited

U.S. PATENT DOCUMENTS

| | | | |
|---|---|---|---|
| 4,468,611 A | 8/1984 | Tward | |
| 5,450,744 A | 9/1995 | Martyn | |
| 5,739,755 A | 4/1998 | Goldenberg | |
| 5,976,461 A | 11/1999 | Kostuck | |
| 5,992,505 A | 11/1999 | Moon | |
| 7,168,256 B2 | 1/2007 | Shedletsky et al. | |
| 8,607,621 B2 | 12/2013 | Verdegan | |
| 9,504,941 B2 * | 11/2016 | Alper ..................... | B63J 4/002 |

(Continued)

FOREIGN PATENT DOCUMENTS

| | | |
|---|---|---|
| JP | S5728940 A | 2/1982 |
| WO | 2009137636A1 A1 | 11/2009 |
| WO | 2014184421 A1 | 11/2014 |

OTHER PUBLICATIONS

Extended European Search Report for International Application No. 17155284.7 dated Jul. 21, 2017, 7 pages.

*Primary Examiner* — Jewel V Dowtin
(74) *Attorney, Agent, or Firm* — Cantor Colburn LLP

(57) ABSTRACT

A heat exchanger monitoring system includes a heat exchanger 11 capable of receiving a flow F of a working fluid therethrough. A first sensor 12 is disposed upstream of the heat exchanger 11 for measuring at least one property of fluid relating to an amount of contaminant material carried by a first flow entering the heat exchanger 11 and configured to output a first sensor signal indicative of the measured property of the fluid. A second sensor 14 is disposed downstream of the heat exchanger 11 for measuring the same property of the fluid relating to an amount of contaminant material carried by a second flow exiting the heat exchanger 11 and configured to output a second sensor signal indicative of the measured property of the fluid.

15 Claims, 2 Drawing Sheets

(56) References Cited

U.S. PATENT DOCUMENTS

| | | | |
|---|---|---|---|
| 9,816,720 B2* | 11/2017 | Zywiak | ............... F24D 19/1084 |
| 9,983,189 B2* | 5/2018 | Perreault | ................... F02C 3/00 |
| 2014/0262202 A1 | 9/2014 | Kouznetsov et al. | |
| 2016/0041138 A1* | 2/2016 | Pycke | ................ G01N 33/0036 |
| | | | 73/31.03 |
| 2016/0146487 A1 | 5/2016 | Zywiak et al. | |

* cited by examiner

HEAT EXCHANGER MONITORING SYSTEM

FOREIGN PRIORITY

This application claims priority to European Patent Application No. 17155284.7 filed Feb. 8, 2017, the entire contents of which is incorporated herein by reference.

TECHNICAL FIELD

The present invention relates to a heat exchanger monitoring system and a method for monitoring a heat exchanger.

BACKGROUND

Heat exchangers are designed to efficiently transfer heat between a working fluid inside the heat exchanger and another fluid, such as the atmosphere, outside the heat exchanger, or between two fluids in primary and secondary circuits within the heat exchanger.

If debris or contaminants enter the working fluid, these can build up on the internal passages of the heat exchanger, reducing its efficiency. The debris may be, for example, metals or plastics that are worn off from the heat exchanger or from other portions of a fluid circuit connected to the heat exchanger. The heat exchanger may have comparatively small cross-sections for the internal tube(s) and often there are changes in direction leading to areas where flow speeds can reduce or stagnate. Consequently, contaminants may more readily get lodged in the heat exchanger than in other parts of the fluid circuit and this leads to a loss in performance. There is also a possibility of loss in heat exchanger performance arising from degradation of the walls of the heat exchanger.

Heat exchangers made using modern techniques, such as additive manufacturing can have less well-understood degradation profiles over time compared to traditionally manufactured heat exchangers. The impact of contaminants may also be less well understood. In some cases, more care may need to be taken to avoid losses in performance from degradation and/or build-up of contaminants, which can lead to increased frequency of maintenance and/or increased frequency of inspection, in some cases involving taking the heat exchanger out of service. This then means that there can be losses in performance for the heat exchanger due to unnecessary maintenance even when there has been no loss in performance due to build-up of contaminants or degradation of the heat exchanger. There is a need to be able to effectively operate heat exchangers including additive manufactured heat exchangers without such unnecessary inspection and maintenance, and without the risk of excessive reductions in heat exchanger performance. In the past, the performance of heat exchangers has been monitored using temperature sensors in order to identify when performance is reducing and thereby predict when maintenance may be required. However, there is still a need for improved monitoring of heat exchangers.

SUMMARY

According to a first aspect, the invention provides a heat exchanger monitoring system comprising: a heat exchanger for receiving a flow of a working fluid therethrough; a first sensor for measuring a property relating to an amount of contaminant material carried by a first flow of fluid entering the heat exchanger and configured to output a first sensor signal indicative of the measured property relating to the amount of contaminant material carried by the first flow of fluid; a second sensor for measuring the same property relating to an amount of contaminant material carried by a second flow of fluid exiting the heat exchanger and configured to output a second sensor signal indicative of the measured property relating to the amount of contaminant material carried by the second flow of fluid; and a monitoring device configured to receive and compare the first and second sensor signals to thereby determine a variation in the property relating to the amount of contaminant material carried by the fluid as it passes through the heat exchanger.

Providing sensors on both the inlet and outlet sides of the heat exchanger allows for accurate monitoring of different types of degradation and sources of contaminants in the fluid flow. If the measured contaminants in the fluid increase through the heat exchanger, this can indicate that the heat exchanger is degrading as material is removed from its internal passages. If the measured contaminants in the fluid decrease through the heat exchanger, this can indicate that contaminants are becoming trapped in the internal passages. Trapped contaminants can clog internal passages or reduce the heat-transfer area of the passages reducing the heat exchanger's efficiency. Depending on the magnitude and/or differential between the first and second signals, the monitoring system may output warnings indicating degradation in the heat exchanger or in a circuit to which it is attached, or indicating a build-up in contaminants in the heat exchanger.

The use of sensors that directly measure the amount of contaminants provides advantages compared to the use of temperature sensors to monitor the heat exchanger performance, since changes in the amount of contaminants can provide an earlier and more accurate indication of potential problems. In addition, this technique can more effectively monitor additive manufactured heat exchangers as well as circuits with other additive manufactured parts since it is possible to more effectively identify small particles that may be eroded from the additive manufactured parts by the working fluid.

Traditionally-manufactured heat exchangers have a long history and a well-understood degradation profile due to contaminant build-up. This means that maintenance scheduling may be based on, for example, hours of operation of the heat exchanger, without the need for any sensors detecting contaminant levels. By contrast, additive manufacturing (also known as 3D printing or rapid manufacturing) is a relatively new technology, and the degradation profiles of heat exchangers that have been manufactured by these processes are less well understood. Consequently, it may be important to monitor contaminant levels for heat exchangers produced by various additive manufacturing methods. There is hence a synergy between the proposed monitoring system and the use of an additive manufactured heat exchanger or a heat exchanger in a circuit with other additive manufactured parts. Hence, the system may include an additive manufactured heat exchanger as the heat exchanger of the first aspect, or the heat exchanger of the first aspect may be in a circuit including at least one additive manufactured part. The present heat exchanger monitoring system may allow engineers to gather knowledge of the degradation profile of components manufactured by additive manufacturing, and also to avoid unnecessary maintenance operations (e.g. maintenance operations that were scheduled according to the degradation profiles of traditionally-manufactured heat exchangers).

Generally, "contaminants" refers to any matter contained within in the working fluid other than the working fluid itself. This may be matter entrained within or mixed within the working fluid, including in some cases matter that is dissolved within the working fluid. In specific instances, "contaminants" may refer to dirt, metal particles (including metal particles worn off internal surfaces of the heat exchanger or components attached thereto), plastic particles (including plastic particles worn off internal surfaces of the heat exchanger or components attached thereto), and/or chemicals in the working fluid. In addition to component degradation, contaminants may also enter the system through leaks.

Any type of sensor suitable for detecting contaminants in a fluid flow may be used. For example, the sensor may detect the inductance, capacitance, resistivity, or conductivity of the fluid. Alternatively or additionally, ultrasound or optical sensors may be used.

Capacitance sensors are generally more sensitive than other types of sensors to the different types of contaminants that are expected to occur in a heat exchanger, such as dirt, metal debris, and plastics.

The sensor outputs may be compared to reference values stored in a reference database. The reference database may be populated with data on what (for example) capacitance is associated with contaminant of type X at concentration Y, for a range of contaminant types X and concentrations Y. Thus, the sensor values may be converted into information concerning what types of contaminant are coming from where in a system incorporating the heat exchanger.

The monitoring device may also record changes in the first and/or second sensor signal over time. In this way the monitoring device can determine changes in the contaminant levels over time. From this information, the cumulative amount contaminants clogging the heat exchanger or the amount of degradation of the passages of the heat exchanger may be calculated. The impact of contaminants may be reduced rate and/or efficiency of the heat exchanger, or changes to pressure drop across the heat exchanger. Monitoring the contaminants at both sides of the heat exchanger may be used to estimate the rate and risk of blockage.

A monitoring device that is linked to the sensors and the reference database may convey either or both of instantaneous information or over-time information to a user. This information can be used to create appropriate maintenance schedules for the heat exchanger, as well as indicating wear of components connected to the heat exchanger which can assist with root cause analysis. The variations in sensor readings with time may also be used to predict future maintenance requirements.

The monitoring device may be programmed with appropriate reasoning logic to determine the severity and impact of sensor readings that deviate from expected values. Other system measurements may be included in the reasoning process. For example, combining pressure, temperature, or flow measurements may be used to determine if the heat exchanger is becoming blocked due to detected contaminants.

The first sensor may be upstream of the heat exchanger in the flow of working fluid, and the second sensor may be downstream of the heat exchanger in the flow of working fluid. The sensors may be completely external to the heat exchanger, for example in flow lines connected to the heat exchanger. This arrangement allows for retrofitting of sensors to obtain the proposed system. Alternatively, the sensors may be coupled to and/or partly within the heat exchanger, for example they may be formed in the inlet or outlet section of the heat exchanger. The sensors may be housed entirely within the heat exchanger. When the heat exchanger, or a part of the heat exchanger, is made by an additive manufacturing process, the housings for the sensors may be formed integrally with the heat exchanger using the additive manufacturing process.

The disclosed heat exchanger monitoring system may be used in an aircraft or land-based vehicle. Traditionally, heat exchangers are given maintenance on a set schedule that usually requires the heat exchanger to be comparatively accessible to maintenance staff.

This has put restrictions on the suitable locations for traditionally-manufactured heat exchangers. It is anticipated that heat exchangers made by additive manufacturing methods may be able to go longer between maintenance sessions. Consequently, the heat exchanger may be placed in a less accessible portion of the vehicle. To determine this in real-world usage, it is necessary to have a heat exchanger monitoring system so that maintenance is only performed when required.

According to a second aspect, the invention provides a method of monitoring a heat exchanger, the heat exchanger being for receiving a flow of fluid, the method comprising: using a first sensor, measuring a property relating to an amount of contaminant material carried by a first flow of a fluid entering the heat exchanger; thereby obtaining a first sensor signal indicative of the measured property relating to the amount of contaminant material carried by the first flow of fluid; using a second sensor, measuring a property relating to an amount of contaminant material carried by a second flow of a fluid exiting the heat exchanger; thereby obtaining a second sensor signal indicative of the measured property relating to the amount of contaminant material carried by the second flow of fluid; and comparing the first and second sensor signals to thereby determine a variation in the property relating to the amount of contaminant material carried by the fluid as it passes through the heat exchanger.

The method may include the use of the monitoring system of the first aspect and thus may use sensors and/or a monitoring device as discussed above. The sensors used in the method may be the same as sensors used in the first aspect. That is, the sensors may detect the inductance, capacitance, resistivity, or conductivity of the fluid, or may be ultrasound or optical sensors.

The method may also comprise converting the sensor signals into information regarding contaminant types and a concentration of one or more contaminant types in the working fluid. This may be done by a reference to a reference database that is populated with data on what (for example) capacitance is associated with contaminants of type X at concentration Y, for a range of contaminant types X and concentrations Y. Thus, the sensor values may be converted into information concerning what types of contaminant are coming from where in a system incorporating the heat exchanger.

The method may comprise outputting a first output signal if the concentration of contaminants measured by the first sensor is greater by a first predetermined amount than the amount of contaminants measured by the second sensor; outputting a second output signal if the concentration of contaminants measured by the second sensor is greater by a second predetermined amount than the concentration of contaminants measured by the first sensor; and outputting a third output signal, or no output signal, if the criteria for outputting the first output signal and second output signal are not met. The first signal may indicate wear of components upstream of the heat exchanger. The second signal may indicate wear is occurring inside the heat exchanger.

The method may also comprise outputting an upstream wear signal if the concentration of contaminants measured by the first sensor is above a predetermined threshold. This may allow a user to be alerted to degradation of an upstream component, regardless of whether the contaminant from said component flows freely through the heat exchanger or gets trapped therein.

The first and second sensor signals may also be monitored over time in order to determine changes occurring during use of the heat exchanger. This may be useful, for example, to determine if maintenance of the heat exchanger is required and/or to predict a future maintenance requirement.

BRIEF DESCRIPTION OF THE DRAWINGS

Certain example embodiments of the present invention will now be described in greater detail by way of example only and with reference to the accompanying drawings in which.

DETAILED DESCRIPTION

Figure 1:
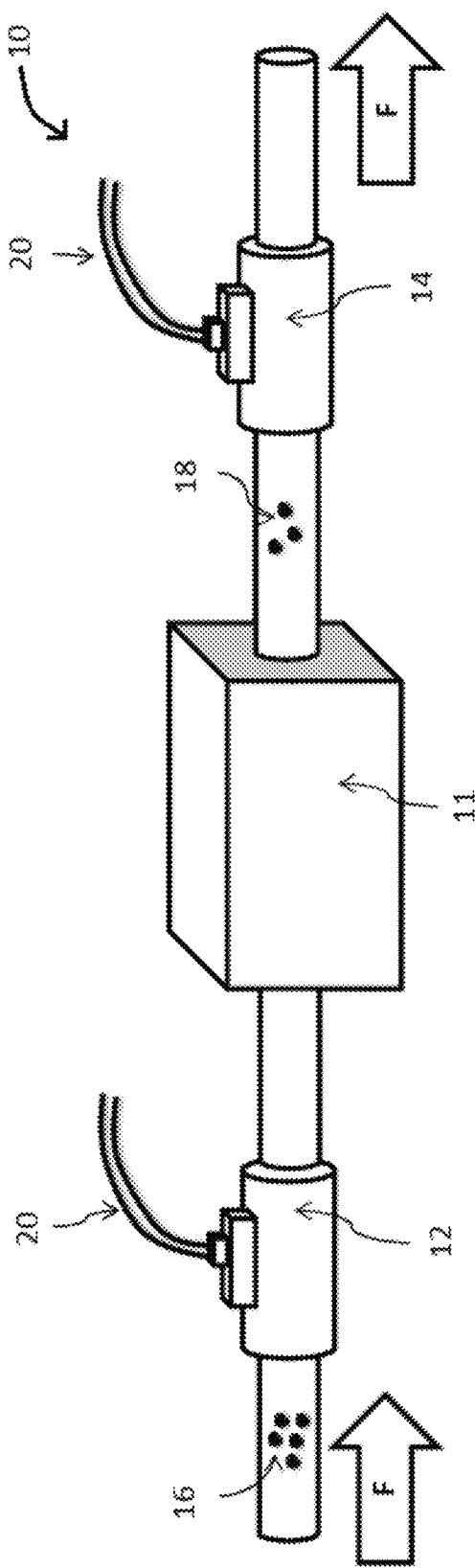
FIG. 1 shows a wired heat exchanger monitoring system.

FIG. 1 shows a heat exchanger monitoring system 10 comprising a heat exchanger 11 and a first sensor 12 on an inlet side of the heat exchanger 11 and a second sensor 14 on an outlet side of the heat exchanger 11. The direction of fluid flow when the heat exchanger is in use is shown by arrow F.

Figure 2:
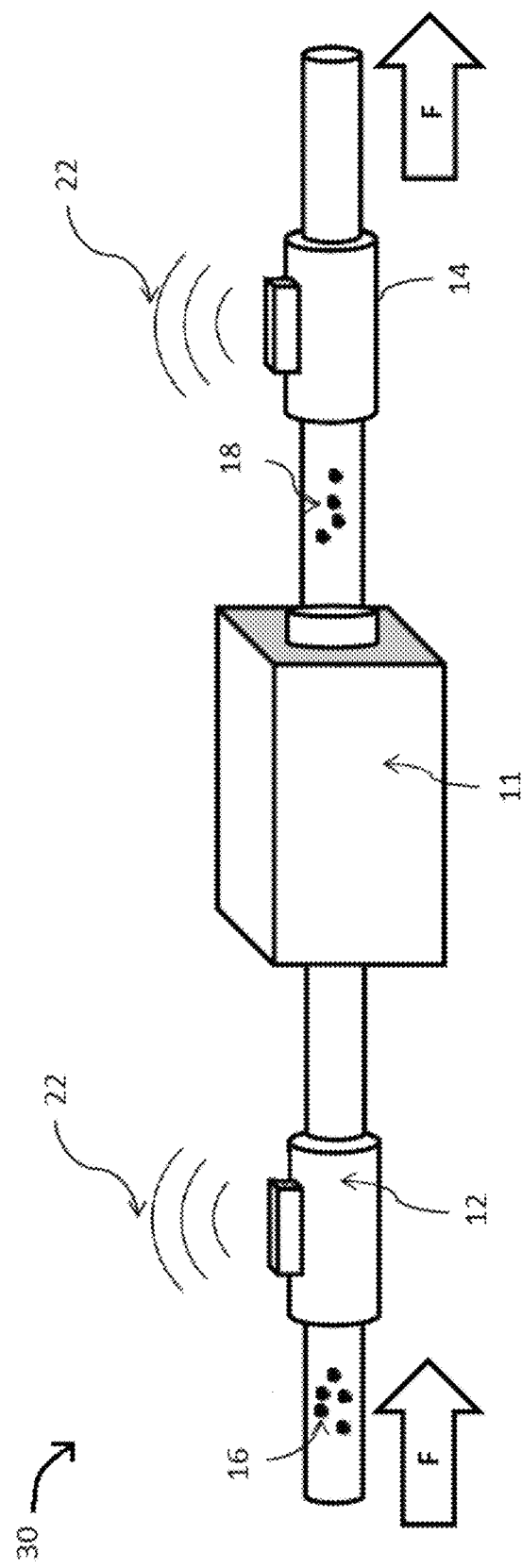
FIG. 2 shows a wireless heat exchanger monitoring system.

The sensors 12, 14 may be connected by a wired connection 20 to a monitoring device. Alternatively, as shown in FIG. 2, either or both of the sensors may have a wireless connection 22 to the monitoring device. The monitoring device may for example be a microcontroller dedicated to the heat exchanger system, or it may be a larger computer system.

The monitoring system monitors readings from the sensors 12, 14. This monitoring system may monitor one or both sensor readings over time and/or may measure differences in the readings between the sensors 12, 14.

The sensors 12, 14 are used to sense contaminants (e.g. an amount of contaminant particles or chemicals) in the fluid flow. Suitable sensors include resistivity, capacitance, conductivity, ultrasound, and optical sensors etc. Capacitance sensors are currently seen to be more sensitive than other types of sensor to the different types of contaminants that are expected to occur in a heat exchanger.

FIG. 1 shows a number of contaminant particles 16 being carried within the fluid into the heat exchanger 11. The first sensor 12 detects the concentration of contaminants (i.e. particles 16) in the fluid passing the sensor 12 and outputs a signal to the monitoring device. That is, the first sensor measures a parameter relating to an amount of contaminant material carried by a first flow.

The fluid then flows through the heat exchanger 11 in which contaminants may become trapped or from which (other) contaminants may be produced.

After passing through the heat exchanger 11, a number of contaminant particles 18 may be being carried within the fluid flowing out of the heat exchanger 11. The second sensor 14 detects the concentration of contaminants (i.e. particles 18) in the fluid passing the sensor 14 and outputs a signal to the monitoring device. That is, the second sensor measures the same parameter as the first sensor relating to an amount of contaminant material carried by a second flow.

Contaminants may build up on the walls inside the heat exchanger 11. In this case, the contaminant concentration should drop through the heat exchanger 11. That is, the first sensor 12 will measure a higher concentration of contaminants than the second sensor 14. Over time, buildup of contaminants within the heat exchanger 11 may reduce its efficiency by blocking flow paths and/or constricting internal cross-sections of the heat exchanger 11 thereby reducing the contact area through which heat may flow between the fluid and the heat exchanger 11.

Alternatively, internal surfaces of the heat exchanger 11 may start to peel off and enter into the fluid flow. In this case, the contaminant concentration will rise through the heat exchanger. That is, the first sensor 12 will measure a lower concentration of contaminants than the second sensor 14.

The monitoring device may contain or otherwise communicate with a reference database. The reference database contains data regarding different known contaminant types and different known contaminant concentrations and may be used to associate these with particular values obtained from the sensors 12, 14. The reference database allows the monitoring device to interpret the signals received from the sensors 12, 14, in terms of contaminant type and/or density. The reference database may also contain information on allowable ranges for degradation in the heat exchanger 11. This information may be used by the monitoring device to alert a user when the heat exchanger 11 requires maintenance or is expected to require maintenance.

The monitoring device may be configured to output a variety of signals based upon the measurement signals it receives from the sensors and how these measurements are interpreted by reference to the reference database.

For example, the monitoring device may output a first signal when the first sensor 12 measures a higher contaminant concentration than the second sensor 14. This may indicate contaminant build-up in the heat exchanger 11. To allow for errors/noise in the sensor readings, a first predetermined threshold may be defined, wherein the monitoring device only outputs the first signal when the first sensor 12 measures a higher contaminant concentration beyond the predetermined threshold than the second sensor 14.

The monitoring device may output a second signal when the first sensor 12 measures a lower contaminant concentration than the second sensor 14. This may indicate wear of the inner surfaces of the heat exchanger 11, such as protective coatings coming loose. Similarly, a second predetermined threshold may be defined to allow for errors/noise in the sensor readings. The first and second predetermined thresholds may be the same or different.

The monitoring device may output a third signal when the first sensor 12 measures the same contaminant concentration than the second sensor 14 (or: the same within the predetermined thresholds). Alternatively, the monitoring device may output no signal at this time because this situation may indicate a stable state where the heat exchanger 11 is experiencing neither form of degradation.

The monitoring device may also track changes in contaminant concentration over time. If, for example, the first sensor 12 senses a generally increasing concentration of contaminants, this may indicate increasing levels of wear in a component upstream of the heat exchanger 11. If the second sensor indicates a generally increasing concentration of contaminants but the first sensor does not indicate this, then this may indicate accelerating wear in the heat exchanger 11.

The sensors 12, 14 shown in the Figures are held in housings that are separate to the heat exchanger and fitted around the flow line that connects to the heat exchanger. In an alternative arrangement, the sensors 12, 14 may each be housed within the heat exchanger, for example at the inlet and outlet portions of the heat exchanger. Heat exchangers made by additive manufacturing may more easily incorporate this housing of the sensors 12, 14 compared to traditionally manufactured heat exchangers.

Where the heat exchanger has more than one working fluid (for example, if it does not simply exchange heat with the ambient air) then a similar arrangement can be used to monitor each of the fluids that flow through the heat exchanger, for example both of primary and secondary fluids.

The invention claimed is:

1. A heat exchanger monitoring system comprising:
   a heat exchanger for receiving a flow of a working fluid therethrough;
   a first sensor for measuring a property relating to an amount of contaminant material carried by a first flow of fluid entering the heat exchanger and configured to output a first sensor signal indicative of the measured property relating to the amount of contaminant material carried by the first flow of fluid;
   a second sensor for measuring the same property relating to an amount of contaminant material carried by a second flow of fluid exiting the heat exchanger and configured to output a second sensor signal indicative of the measured property relating to the amount of contaminant material carried by the second flow of fluid; and
   a monitoring device configured to receive and compare the first and second sensor signals to thereby determine a variation in the property relating to the amount of contaminant material carried by the fluid as it passes through the heat exchanger.

2. A heat exchanger monitoring system as claimed in claim 1 comprising a reference database containing values for converting the sensor signals into information regarding one or more contaminant types and a concentration of the one or more contaminant types in the working fluid.

3. A heat exchanger monitoring system as claimed in claim 2, wherein the monitoring device is configured to output:
   a) a first output signal if the concentration of contaminants measured by the first sensor is greater by a first predetermined amount than the amount of contaminants measured by the second sensor;
   b) a second output signal if the concentration of contaminants measured by the second sensor is greater by a second predetermined amount than the concentration of contaminants measured by the first sensor; and
   c) a third output signal, or no output signal, if the criteria for outputting the first output signal and second output signal are not met.

4. A heat exchanger monitoring system as claimed in claim 2, wherein the monitoring device is configured to output an upstream wear signal if the concentration of contaminants measured by the first sensor is above a predetermined threshold.

5. A heat exchanger monitoring system as claimed in claim 1, wherein the monitoring device is arranged to record changes in the first and/or the second sensor signal over time.

6. A heat exchanger monitoring system as claimed in claim 1, wherein the first and second sensors are capacitive sensors.

7. A heat exchanger monitoring system as claimed in claim 1, comprising:
   a first housing for receiving the first sensor and a second housing for receiving the second sensor.

8. A heat exchanger monitoring system as claimed in claim 7, wherein the first and second housings are each located on a flow line external to the heat exchanger.

9. A heat exchanger monitoring system according to claim 1, wherein the heat exchanger is at least partially constructed by an additive manufacturing method.

10. A heat exchanger monitoring system according to claim 9 wherein housings for the first and second sensors are integrally formed with the heat exchanger.

11. A method of monitoring a heat exchanger, the heat exchanger being for receiving a flow of fluid, the method comprising:
    using a first sensor, measuring a property relating to an amount of contaminant material carried by a first flow of fluid entering the heat exchanger;
    thereby obtaining a first sensor signal indicative of the measured property relating to the amount of contaminant material carried by the first flow of fluid;
    using a second sensor, measuring a property relating to an amount of contaminant material carried by a second flow of fluid exiting the heat exchanger;
    thereby obtaining a second sensor signal indicative of the measured property relating to the amount of contaminant material carried by the second flow of fluid; and
    comparing the first and second sensor signals to thereby determine a variation in the property relating to the amount of contaminant material carried by the fluid as it passes through the heat exchanger.

12. A method of monitoring a heat exchanger as claimed in claim 11, comprising:
    converting the sensor signals into information regarding one or more contaminant types and a concentration of the one or more contaminant types in the working fluid.

13. A method of monitoring a heat exchanger as claimed in claim 11, comprising:
    outputting a first output signal if the concentration of contaminants measured by the first sensor is greater by a first predetermined amount than the amount of contaminants measured by the second sensor;
    outputting a second output signal if the concentration of contaminants measured by the second sensor is greater by a second predetermined amount than the concentration of contaminants measured by the first sensor; and
    outputting a third output signal, or no output signal, if the criteria for outputting the first output signal and second output signal are not met.

14. A method of monitoring a heat exchanger as claimed in claim 11, comprising:
    outputting an upstream wear signal if the concentration of contaminants measured by the first sensor is above a predetermined threshold.

15. A method of monitoring a heat exchanger as claimed in claim 11, comprising:
    monitoring the first and/or the second sensor signal over time and recording changes in the sensor signals with time.

* * * * *